United States Patent
Whitehurst (12) 
(10) Patent No.: US 6,623,634 B1
(45) Date of Patent: Sep. 23, 2003

(54) TISSUE FLOAT WATER BATH LINER AND FILTER

(76) Inventor: Paul L. Whitehurst, 3502 Millvale, NE., Canton, OH (US) 44705

(*) Notice: Subject to any disclaimer, the term of this patent is extended or adjusted under 35 U.S.C. 154(b) by 268 days.

(21) Appl. No.: 09/685,566

(22) Filed: Oct. 11, 2000

(51) Int. Cl.[7] .......... B01D 29/05; B01D 35/04; B01D 35/18; G01N 1/28
(52) U.S. Cl. .......... 210/186; 210/232; 210/474; 210/482; 210/483; 210/484; 422/101
(58) Field of Search .............. 210/186, 473, 210/482, 483, 484, 232, 474; 422/101

(56) References Cited

U.S. PATENT DOCUMENTS

| | | | |
|---|---|---|---|
| 1,594,400 A | * | 8/1926 | Wuest |
| 2,367,794 A | * | 1/1945 | Marselus |
| 2,477,404 A | | 7/1949 | Butt, Jr. |
| 2,997,814 A | | 8/1961 | Brandt |
| 3,103,844 A | | 9/1963 | Persson |
| 3,272,348 A | | 9/1966 | Metz |
| 3,849,312 A | | 11/1974 | Wecker, Sr. |
| 4,043,916 A | | 8/1977 | Wecker, Sr. |
| 4,321,139 A | | 3/1982 | Auclair |
| 4,377,476 A | | 3/1983 | Ferrara |
| 5,364,597 A | | 11/1994 | Polk, Jr. et al. |
| 5,532,168 A | | 7/1996 | Marantz |
| 5,837,198 A | | 11/1998 | Itani |

OTHER PUBLICATIONS

Filter Holders and Funnels, HPLC–Accessory Products.
Miscellaneous Filter ADS FIL 10083,9894 and 9904.
Industrial Filtration of Liquids, pp. 109, 300, 306, 308 and 320.

* cited by examiner

Primary Examiner—Thomas M. Lithgow
(74) Attorney, Agent, or Firm—Jacobson Holman PLLC

(57) ABSTRACT

A liner and filter for filtering a heated tissue float water bath is described. In one embodiment, the liner and filter are a disposable one piece unit. In another embodiment, the liner and filter are two separate components and only the filter is disposable. The filter has a flat microcloth bottom and a plurality of support members extending across the flat microcloth bottom for sandwiching the microcloth there between to form the filter. The liner has a generally vertical wall with an outwardly extending top flange for positioning the liner and filter into the bath container and for easy removal. When the liner and filter are removed, the assembly carries with it any loose tissue fragments, paraffin or other contaminants, thus leaving the bath water clean and ready for reuse. The liner and filter can be circular, square or rectangular depending on the shape of the tissue float water bath container in which the invention is to be used.

16 Claims, 5 Drawing Sheets

TISSUE FLOAT WATER BATH LINER AND FILTER

BACKGROUND OF THE INVENTION

1. Field of the Invention

The present invention pertains generally to a disposable liner and filter assembly and, more specifically, to a disposable liner and filter assembly for a tissue float water bath used in histological procedures.

2. Description of the Prior Art

Figure 1:
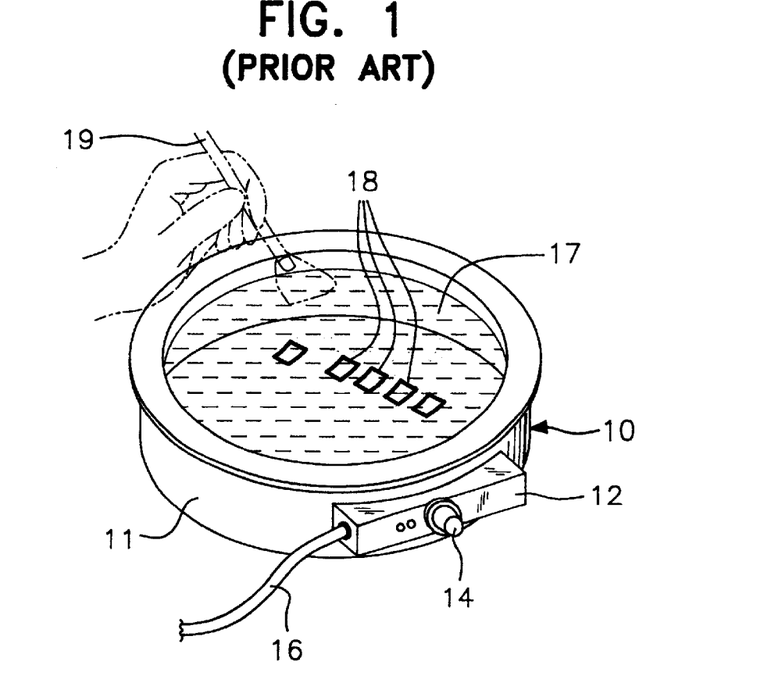
FIG. 1 is a perspective view of a conventional tissue float water bath container with heating element and bath water partially filling the container.
Figure 2:
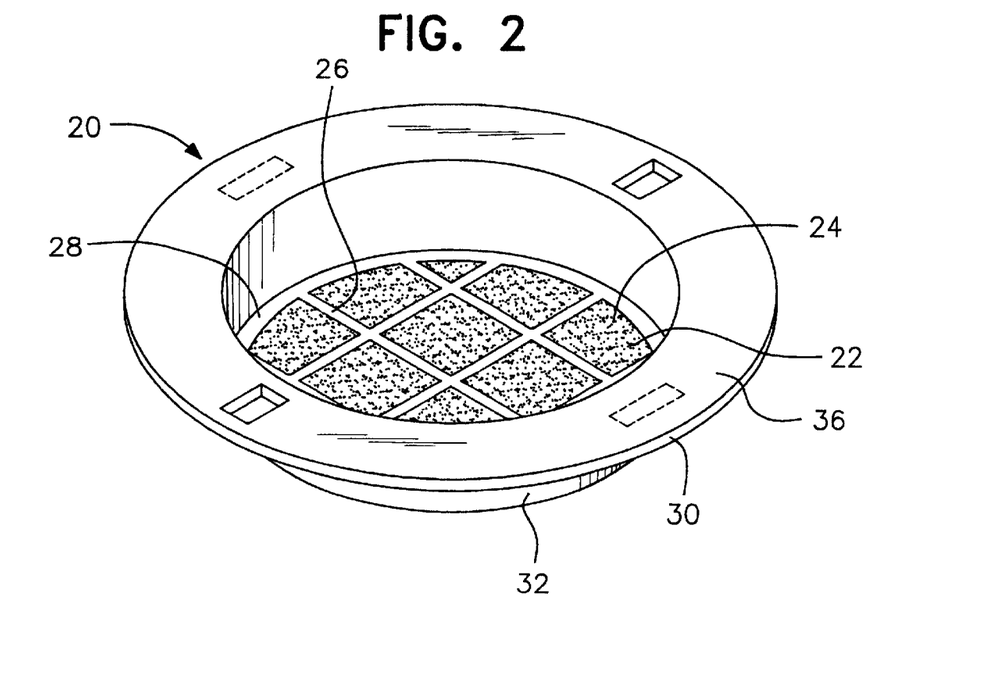
FIG. 2 is a perspective view of a disposable one-piece circular tissue float water liner and filter according to a first embodiment of the invention.

Referring to FIG. 1, a conventional tissue float water bath container is shown, and is generally indicated by reference numeral 10. The bath container 10, as shown, has a generally cylindrical shape and a heating element 12 mounted in the side wall 11. The heating element 12 has a control knob 14 for adjusting the temperature and is connected to an electrical power source by way of cord 16. The container 10 is partially filled with bath water 17 and the heating element 12 serves to heat the container 10 so as to heat and maintain the bath water 17 at the desired warm temperature. A plurality of tissue ribbon sections 18 are shown floating on the surface of the bath water 17 in the bath container 10.

The initial procedure for placing a tissue ribbon into the bath water is by lowering one end in first. The remainder of the ribbon is lowered gradually with a slight pull until the ribbon is in the heated bath water. Using a heated tissue separator 19 (shown in dashed lines), the sections 18 can be easily and uniformly separated from each other. Overheating or under-heating of the bath water 17 must be avoided. Such temperature changes in the bath water can cause a loss of the valuable ribbon sections 18.

It is also important to insert clean, dust free slides into the flotation water bath. With the aid of a camel's hair brush, the section is oriented so that it is centrally placed on the slide allowing free margins for subsequent coverslipping and labeling.

The drawback to this procedure, as is commonly known and performed in the field of histology, is that fat tissue and other tissue fragments not properly fixed to the ribbon will immediately fragment and scatter very rapidly upon contact with the warm bath water. This often makes it impossible to retrieve a sufficient microscopic paraffin section. When the water is thus contaminated, something must be done because further use of the contaminated bath water will be disruptive to future procedures utilizing the same bath water.

Normally, at this point, the proper procedure is to discard the bath water, because it is contaminated. Additionally, the bath container must be cleaned, the water prepared again to the required temperature and the necessary chemical(s) added. This water replacement procedure is very time consuming. Also, this type of interruption can occur on several occasions each day. Hence, this critical procedural step is often neglected by technicians due to the time involved in the water replacement. Obviously, then, tissue fragments remain in the contaminated bath water. These fragments can be easily transferred onto another patient's slides without noticing. This is a problem and can be very critical under microscopic examination. Accordingly, there is a need in the industry for a device that eliminates the often neglected step of completely discarding and replenishing the bath water from the container 10 after every contamination, yet allows the technician to easily and safely clean the bath water 17 and container 10 in the shortest time to eliminate contamination.

The patent art discloses various screens and filtering devices for biological fluids. The Ferrara U.S. Pat. No. 4,377,476 discloses in FIG. 4 a tissue filtering bath for histology which includes a removable tray-like strainer with a porous bottom. According to the patent, the strainer may be disposable. The Itani U.S. Pat. No. 5,837,198 discloses in FIGS. 3 and 11 a container used in tissue treatment which includes a cylindrical side wall and nylon mesh bottom. Other prior U.S. patents which disclose tissue treating baths and/or disposable filters include the following:

| | | |
|---|---|---|
| 2,477,404 | 3,272,348 | 4,321,139 |
| 2,997,814 | 3,849,312 | 5,364,597 |
| 3,103,844 | 4,043,916 | 5,532,168 |

However, the prior art patents do not disclose a liner and filter assembly used in a histology treatment bath which is either totally disposable or filter disposable, or has a structure which can be conveniently used and inexpensively manufactured.

SUMMARY OF THE INVENTION

In order to overcome the above drawbacks in the prior art structures, the present invention is directed toward a disposable liner and filter for conventional histology water baths that is convenient, inexpensive and easy to use. The liner preferably includes a relatively short vertical wall in the shape of a cylinder or square, depending upon the configuration of the conventional histology bath container. The liner is sized to fit neatly inside the bath container wall and includes a generally horizontal rim or flange extending outwardly from the vertical wall. The rim or flange then extends over and rests on the top of the bath container wall to maintain the liner and filter in position in the bath and bath water. Preferably, the liner top rim or flange can have at least one attachment means for securing the removable liner and filter to the top wall of the tissue float water bath container. In one preferred form, the attachment means is an adhesive tab on the underneath side of the top rim or flange.

The filter portion of the present invention comprises a generally horizontal bottom wall adjacent the lower edge of the liner vertical wall. The filter bottom is preferably made of microcloth material and includes a reinforcing outer rim and a plurality of support members extending crosswise across the flat filter bottom for sandwiching the microcloth filter therebetween and providing support for the central portion of the filter.

In one embodiment, the liner and filter is a single disposable unit. The liner, flange and support members are preferably made of thin cardboard treated to withstand warm fluids for a lengthy period of time, such as for example the materials used for hot drinking cups and the like. The filtering paper is standard microcloth such as used for gelatinous grindates and rapid filtering. In operation, the operator merely places the liner and filter in position within the bath, fills and heats the container with the bath water. After use, the liner and filter are removed, carrying with them any loose tissue fragments, paraffin or other contaminants, thus leaving the bath water clean. Another disposable liner and filter can then be inserted into the bath water, and the next histology procedure performed.

In a second embodiment, the liner and filter are two separate pieces. The liner and outwardly extending horizontal rim or flange are one piece and the horizontal bottom filter is a separate second piece. The liner is provided with an inwardly projecting lip around its bottom edge on which the bottom filter rests. Depending upon whether the conventional histology water bath is cylindrical, rectangular or square, the liner and separate disposable filter are correspondingly circular, rectangular or square in shape. After use, the liner and disposable filter are removed, carrying with them any loose tissue fragments, paraffin or other contaminants. The liner is cleaned and the disposable filter replaced. In this embodiment, the liner can be made of any durable hard type of plastic or other rigid material for permanent use in conjunction with replaceable sheet-like filters.

The liner and filter assemblies of the present invention reduce downtime and save the technician considerable time in eliminating the need to dispose of contaminated water, clean the bath container and refill and reheat fresh water. Further, the risk of contamination is eliminated. Thus, safety to the patient and tissues is increased.

It is therefore an object of the present invention to provide a disposable liner and filter for use in conventional it tissue float water baths for filtering the tissue float bath water upon removal.

It is a further object of the present invention to provide a disposable liner and filter in accordance with the preceding object which will avoid the necessity of repeatedly discarding and replenishing the bath water each time it becomes contaminated during a histological procedure.

Another object of the present invention is to provide a liner and filter in accordance with the preceding objects which has a flat microcloth bottom that is supported adjacent the lower edge of the liner.

A further object of the present invention is to provide a liner and filter in accordance with the preceding object in which the bottom filter includes an outer rim extending completely around the microcloth bottom and a plurality of support members extending in a crisscross pattern from the bottom rim and across the microcloth bottom for sandwiching the microcloth bottom therebetween and providing support to the filtering means.

A still further object of the present invention is to provide a liner and filter in accordance with the preceding objects and which is made in a plurality of shapes and sizes depending on the shapes and sizes of the conventional water bath containers in use.

It is yet another object of the present invention to provide in one embodiment an inexpensive liner and filter of one piece construction which can be removed from the water bath and carry with it all water contaminants so that the bath water can be reused.

Still another object of the present invention is to provide in another embodiment an inexpensive liner and filter of two piece construction which can be removed from the water bath and carry with it all water contaminants so that the bath water can be reused and the liner can be reused after cleaning with a new bottom filter.

Still yet a further object of the present invention is to provide a disposable liner and filter which will conform to conventional forms of manufacture and provide a device that will be disposable, economically feasible and relatively trouble free in use.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Although only a few preferred embodiments of the invention are explained in detail, and it is to be understood that the embodiments are given by way of illustration only. It is not intended that the invention is to be limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity. It is to be understood that each specific term includes all technical equivalents which operate in a similar manner to accomplish a similar purpose.

A first embodiment of the present invention is now described in detail by initially referring to FIGS. 2, 3, 4 and 5. The liner and filter of the present invention is shown and generally indicated by reference numeral 20 and is for filtering the bath water in a tissue float water bath container, such as container 10. The liner and filter 20 includes a generally vertical liner 30 and a bottom wall filter 22 for filtering the tissue float water bath.

Figure 4:
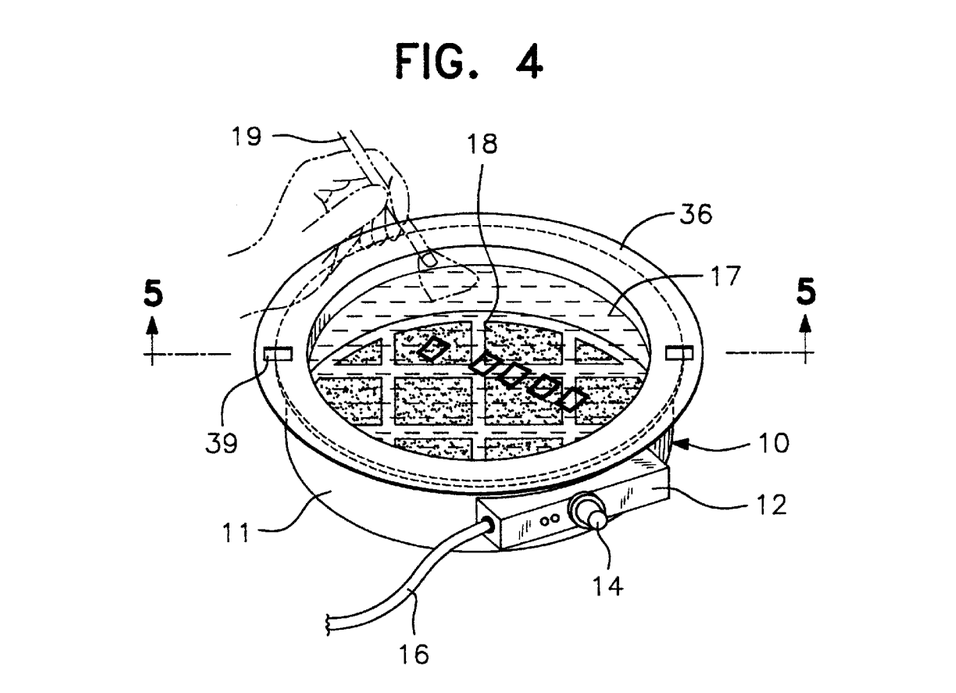
FIG. 4 is a perspective view of the tissue float water liner and filter shown in FIG. 2, when positioned in the conventional water bath container with heating element.

The liner and filter 20 is generally cylindrical and sized to fit neatly around the inside of the cylindrical vertical wall 11 of the container 10. A generally horizontal flange or rim 36 extends outwardly from the top of the vertical wall 32, which extends over and rests on the top of the bath container wall 11 to maintain the liner and filter 20 in position in the bath. When positioned in the bath, as shown in FIG. 4, the bottom wall filter 22 is positioned adjacent the bottom of the container 10 so that substantially all of the bath water 17 is positioned above the bottom wall filter 22.

The bottom wall filter 22 includes a flat microcloth element 24. The flat microcloth element 24 allows or permits the bath water to flow in and out through the filter 22. Across the flat microcloth element 24 are a plurality of support members, generally indicated by reference numeral 26, which extend across the flat microcloth 24. In the preferred form, the support members 26 are in a perpendicular crisscross shaped pattern. The members 26 support the microcloth element 24 by sandwiching the microcloth element 24 therebetween. A bottom rim 28 preferably extends completely around the microcloth element 24 for connecting the ends of the support members 26 to the lower edge of the liner, as shown in FIG. 3.

The liner top flange 36 is made to protrude over the wall 11 of the bath water container 10. When resting on the top of wall 11, this flange 36 positions the removable liner 30 so as to fit snugly in the tissue float water bath container 10. Also, because the flange 36 extends or projects over the container wall 11, the user has a means to lift the device 20 out of the container 10 without touching the bath water or the container 10. Accordingly, further contamination is avoided.

Figure 3:
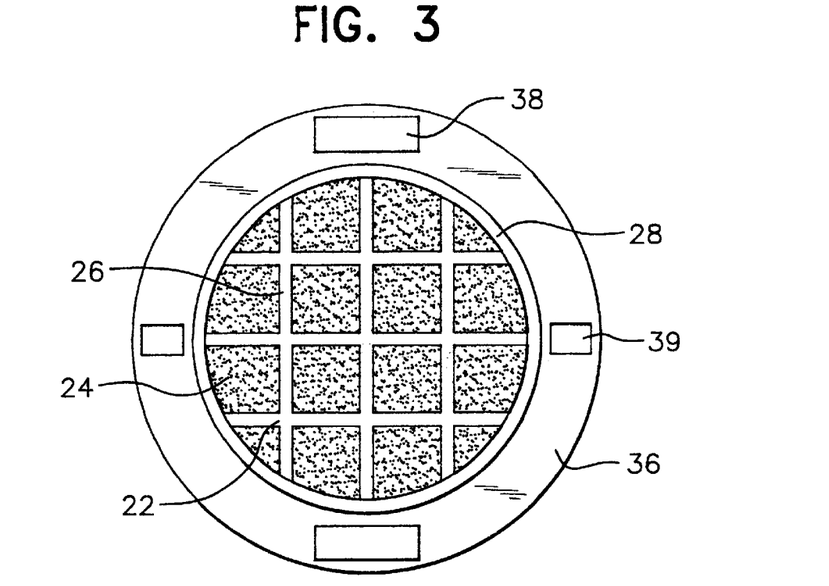
FIG. 3 is a bottom view of the disposable circular tissue float water liner and filter shown in FIG. 2.

A plurality of adhesive type tabs 38 can be positioned on the bottom side of the liner flange 36 as shown in the bottom view of the liner and filter 20 in FIG. 3. These tabs 38 are used to secure the liner 30 to the top of wall 11 of water bath container 10 when in use. Additionally, it has been contemplated to add a plurality of cutout areas 39 along the top flange 36. These cutouts 39 can be for some water bath containers 10 which use lock bolts. Thus, the liner and filter 20 can fit over the lock bolts and secure the liner and filter to the bath.

Figure 5:
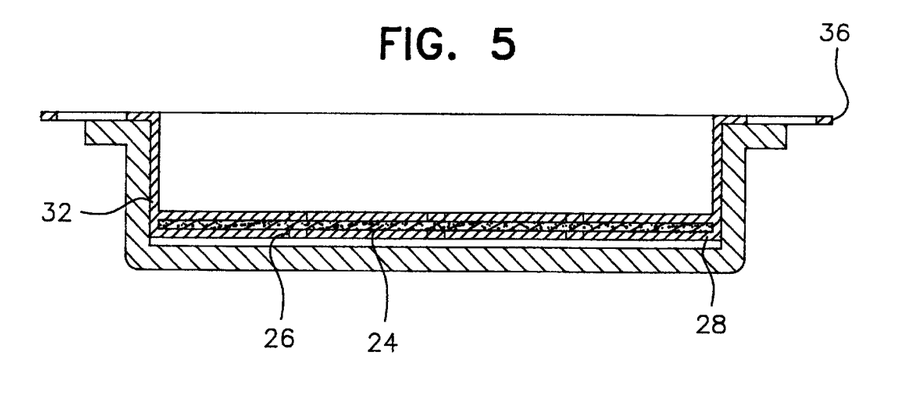
FIG. 5 is a sectional view of FIG. 4 taken along line 5—5.

Referring specifically to FIG. 4, the assembly 20 is shown snugly fitting into the water bath container 10. This confines any floating paraffin ribbon or other contaminates within the filter area. FIG. 5 is a cross sectional view taken along 5—5 of FIG. 4. The filter microcloth 24 is preferably of the type used for gelatinous grindates and rapid filtering. The microcloth 24 is secured between two layers of strips forming the plurality of support members 26 and showed as a crisscross type pattern for support.

In this embodiment, the liner 30 and bottom wall filter 22 are a single one-piece disposable unit. The liner 30, flange 36, support members 26 and rim 28 are preferably made of thin cardboard material treated to withstand warm fluids for a lengthy period of time, such as for example the materials used for hot drinking cups and the like.

In use, the operator merely places the liner and filter assembly 20 in position within the bath container 10, fills the container with the bath water, and heats the bath water to the desired temperature. After use, the liner and filter are removed as one single piece, carrying with them any loose tissue fragments, paraffin or other contaminants, thus leaving the bath water clean. Another disposable liner and filter can then be inserted into the bath water as the water flows through the bottom wall filter, and the next histology procedure can be performed without having to refill and reheat fresh bath water.

Figure 6:
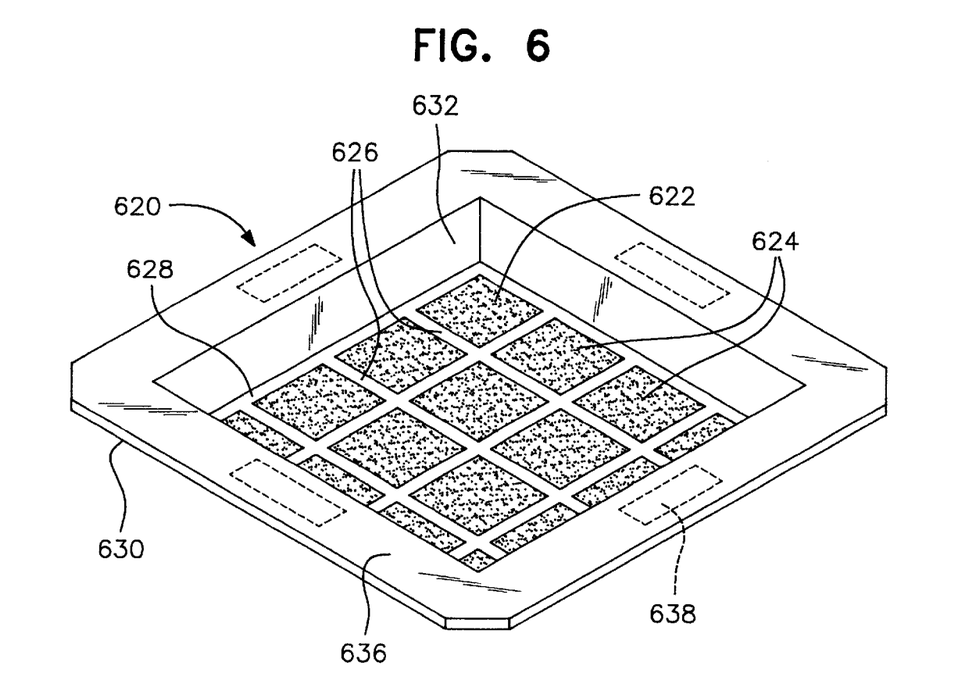
FIG. 6 is a perspective view of a disposable one-piece tissue float water liner and filter according to the first embodiment of the invention but having a square shape.

Referring now to FIG. 6, the liner and filter shown is a square unit generally indicated by reference numeral 620. The assembly 620 is designed for use in a square shaped tissue float water bath container. The liner and filter 620 is a one-piece assembly with bottom wall filter 622 for filtering the tissue float bath water. The filter 622 includes a flat microcloth bottom element 624. Across the flat microcloth bottom 624 are a plurality of support members, generally indicated by reference numeral 626. The plurality of support members 626 extend across the flat microcloth bottom 624. The members 626 support the microcloth bottom 624 by sandwiching the microcloth 624 therebetween. A square-shaped bottom rim 628 extends completely around the microcloth bottom 624 and connects the plurality of support members 626 to form the bottom filter 622. The liner 630 also includes a liner top flange 636 connected to the square shaped wall and extends outwardly from the wall 632 and perpendicular thereto. A plurality of adhesive type tabs 638 are optionally included on the bottom side of the liner top rim 636. These tabs 638 are used to secure the liner 630 to the water bath container wall when in use.

Figure 7:
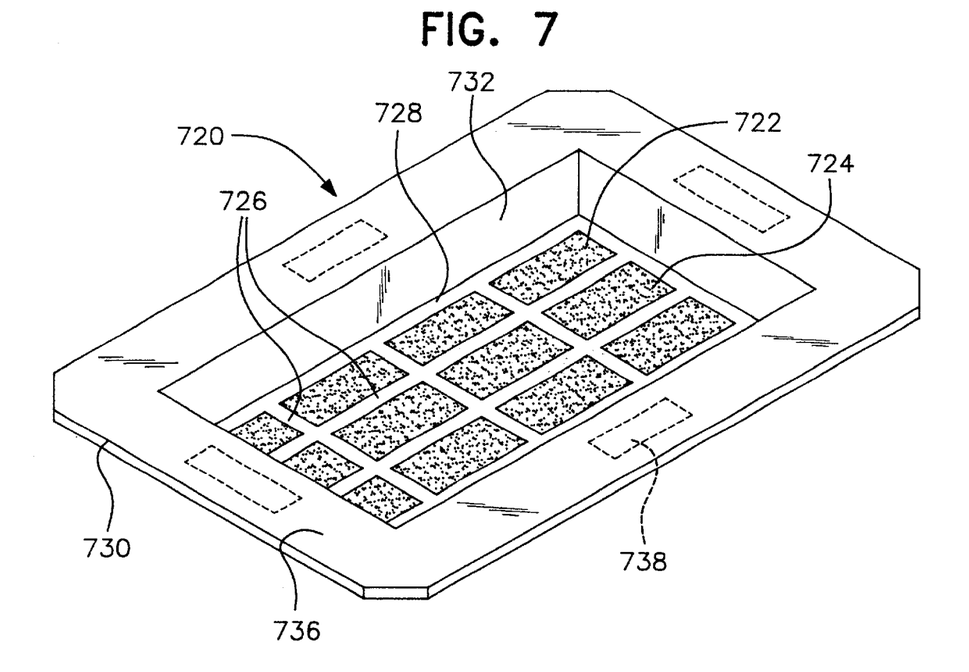
FIG. 7 is a perspective view of a disposable one-piece tissue float water liner and filter according to the first embodiment of the invention but having a rectangular shape.

Referring next to FIG. 7, the liner and filter shown is a rectangularly shaped unit generally indicated by reference numeral 720. The assembly 720 is also a one-piece disposable unit for use with a rectangularly shaped tissue float water bath container. The assembly includes a rectangular vertical liner wall 730 with an outwardly extending horizontal flange 736 and a bottom wall filter 722 for filtering the tissue float bath water. The filter 722 includes a flat microcloth element and a plurality of support members 726, which extend across the flat microcloth bottom 724. The members 726 support the microcloth bottom 724 by sandwiching the microcloth bottom 724 therebetween. Bottom rim 728 extends completely around the microcloth bottom 724 and connects the plurality of support members 726 to form the complete bottom filter 722. The liner 730 also includes a liner top flange 736 connected to the rectangular shaped liner wall 732 and extends outwardly from the wall 732 perpendicular thereto. A plurality of adhesive type tabs 738 are optionally included on the bottom side of the liner top flange 836 to secure the liner 730 to the top wall of a water bath container if desired.

Figure 8:
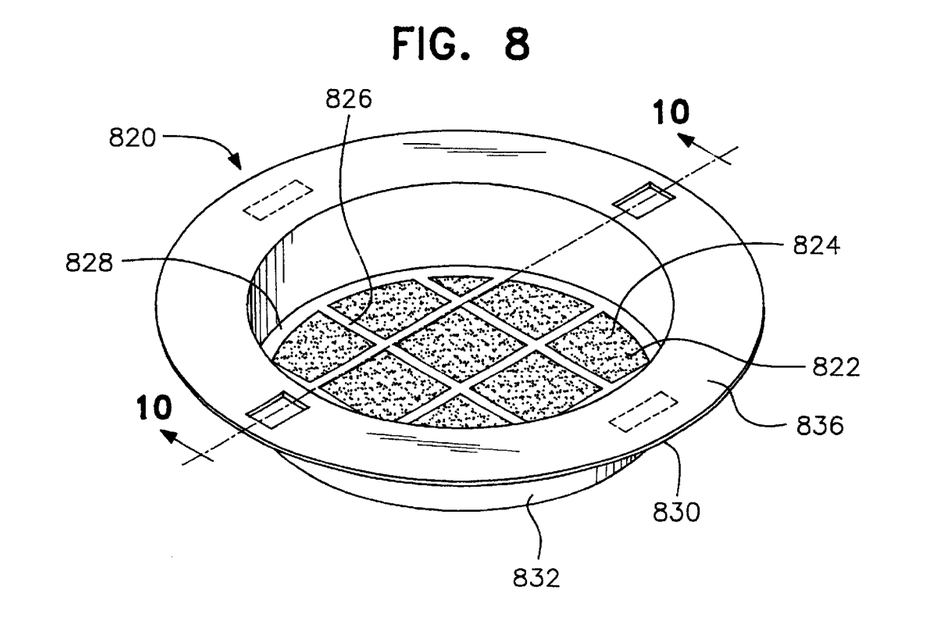
FIG. 8 is a perspective view of a liner and filter according to a second embodiment of the present invention in which a disposable bottom filter is separable from a reusable liner.
Figure 9:
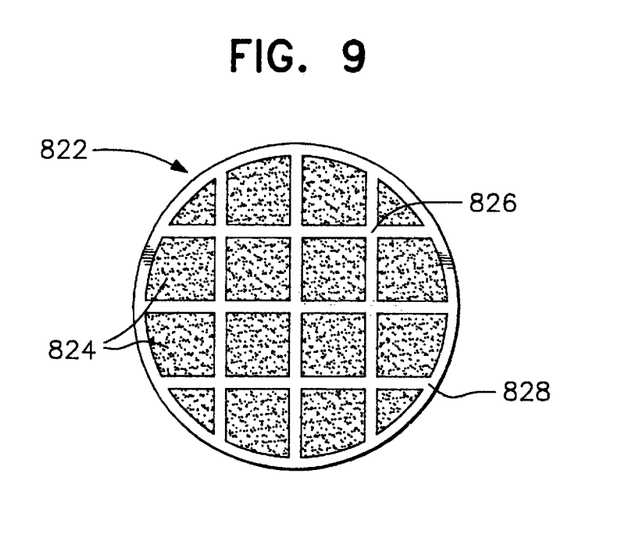
FIG. 9 is a top view of the disposable circular tissue float water filter separated from the liner according to the second embodiment of the invention.
Figure 10:
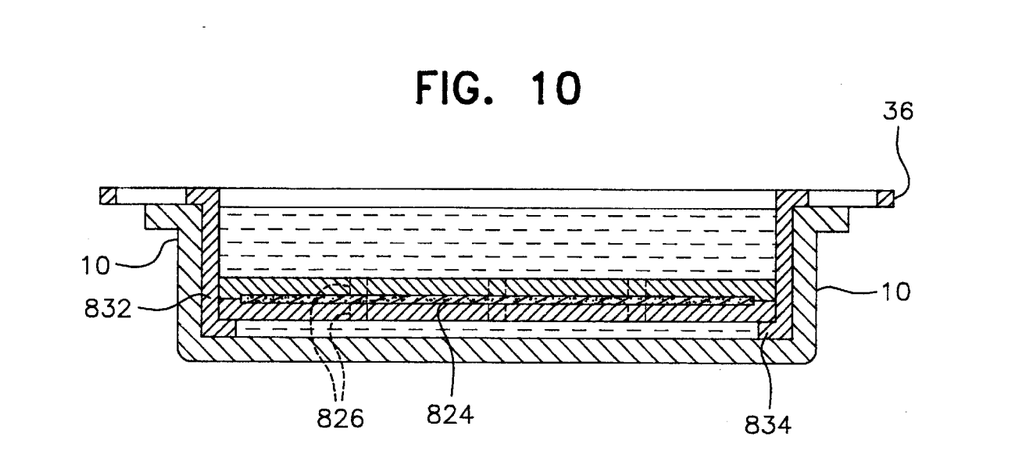
FIG. 10 is a sectional view of FIG. 8 taken along line 10—10.

Turning now to the second embodiment, as illustrated in FIGS. 8, 9 and 10, there is shown a two piece liner and filter generally designated by the numeral 820. The assembly 820 includes a separate liner 830 having a vertical wall 832 in the shape of a cylinder. The liner 830 is sized to fit neatly inside the bath container 10 and snug the inside of the wall 11. The liner 830 includes a generally horizontal rim or flange 836 which extends outwardly from the vertical wall 832. The rim or flange 836 extends over and rests on the top of the bath container wall 11 to maintain the liner and filter 820 in position in the bath 10.

The cylindrical wall 832 includes a inwardly projecting liner bottom rim 834 around its lower edge, which is preferably perpendicular to the wall 832. The liner bottom rim 834 serves to support a separate and removable filter generally designated by reference numeral 822. The filter 822 is constructed in a manner similar to the bottom filters of the previously described one piece assemblies. More specifically, the filter 822 preferably includes a flat microcloth element 824 and a plurality of support members, generally indicated by numeral 826. See FIG. 9. The support members 826 extend across both sides of the flat microcloth 824, preferably in a perpendicular, crisscross pattern to support and retain the microcloth filter means. An outer rim 828 preferably extends completely around the microcloth element 824 to provide a rigid support for the filter element 822 on the supporting liner rim or ledge 834.

In this embodiment of the invention, the separate liner 830 is preferably made of a durable hard plastic or other suitable material for permanent reusable use. On the other hand, the support elements of the bottom filter 822, including the crisscross support members 826 and outer rim 828, are preferably made of a cardboard or similar type inexpensive material which can be readily formed on both sides of the flat microcloth 824. The outside dimension of the bottom rim 828 is sized to frictionally fit within the inside surface of the side wall 832 of the rigid liner 830 and can, thus, be held against the inwardly extending lip or rim 834 by the frictional fit.

Because the assembly 820 is made as two separate parts, the filter 822 can be removed by merely applying light pressure from the bottom side of the filter 822 and releasing it from under the friction fit or pressure type fit. Of course, an adhesive could be added to secure the filter 822 in the liner 830 or another type of holding means on the interior walls 832 or bottom rim 834 could be employed. The attachment of the two pieces is only limited by the ability to release the filter 822 from the plastic liner 830 so that the filter 822 can be readily replaced and the downtime minimized. As can be appreciated, other types of securing means can be used such as notches on the interior wall or walls of the liner 830, so that the filter 822 snaps into place. Once the filter 822 is separated from the liner 830, the filter 822 can be discarded and the liner 830 can be cleaned with hot water and ready for reuse with another filter.

As described above, the liner 830 and filter 822 are two separate pieces; the liner wall 830 with outwardly extending horizontal support flange 836 comprises one piece and the horizontal bottom filter 822 comprises a separate second piece. The liner 830 also includes the inwardly projecting lip or rim 834 around its bottom edge on which the bottom filter 822 rests. After use, the liner 830 and disposable filter 822 are removed, carrying with them any loose tissue fragments, paraffin or other contaminants. The liner 830 is cleaned and the disposable filter 822 replaced.

Although not illustrated in the drawings, it will be apparent to those skilled in the art that the one piece square and rectangular liner and filter assemblies as illustrated in FIGS. 6 and 7, respectively, can be made in two pieces, similar to the circular or cylindrical liner and filter 820, shown in FIGS. 8–10. The bottom filter 622 or 722 can be made as a single separable piece from the liner 630 or 730, in the same manner as described for separable bottom filter 822 from liner 830.

Although not preferred, the liner and filter of the present invention could be constructed with one or more portions of the vertical wall of the liner having microcloth filter sections, if additional filter sections are desired. Such an arrangement is best suited for the one piece liner and filter construction.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed is:

1. An apparatus for filtering a tissue float water bath in a heated container, said apparatus comprising:
   a removable filter for filtering said tissue float water bath, said filter having a generally flat microcloth bottom;
   a plurality of support members extending across said flat microcloth bottom for sandwiching said microcloth sandwiching said microcloth bottom therebetween and providing support to said filter;
   a bottom rim extending completely around said microcloth bottom and connecting to said plurality of support members;
   a removable liner for lining said tissue float water bath, said liner having a sidewall shape generally to correspond to a shape of said water bath and connected to said bottom rim of said removable filter; and
   a liner top rim connected to said liner side wall and extending outwardly for positioning said liner in said tissue float water bath.

2. The apparatus for filtering the tissue float water bath container as recited in claim 1, wherein said plurality of support members form a crisscrossed shaped pattern.

3. The apparatus for filtering the tissue float water bath container as recited in claim 1, wherein said liner top rim comprising:
   at least one top attachment means for securely attaching said removable liner to said tissue float water bath; and
   at least one bottom attachment means for attaching said removable liner to said filter.

4. The apparatus for filtering the tissue float water bath container as recited in claim 3, wherein said at least one attachment means for securely attaching said removable liner to said tissue float water bath, comprising:
   an adhesive tab for securing the liner to the container.

5. The apparatus for filtering the tissue float water bath container as recited in claim 1, wherein said removable filter being circularly shaped.

6. The apparatus for filtering a tissue float water bath as recited in claim 1, wherein said liner bottom rim being circularly shaped.

7. The apparatus for filtering the tissue float water bath container as recited in claim 1, wherein said liner top rim being circularly shaped and larger than said liner bottom rim.

8. In combination, a tissue float water bath container having an interior wall and bottom and a liner and filter which comprises:
   a liner having a generally vertical wall which is sized to fit within said container interior wall;
   a generally horizontal bottom filter supported by said liner adjacent a bottom edge of said liner wall to position said bottom filter adjacent said container bottom; and
   a plurality of support members extending across said bottom filter to provide support to said filter.

9. The combination as defined in claim 8, wherein said container includes a generally vertical wall and said liner includes a generally horizontal outwardly extending flange which rests on said container wall to position said bottom filter adjacent said container bottom.

10. The combination as defined in claim 8, wherein said liner and filter are constructed of one piece and disposable.

11. The combination as defined in claim 8, wherein said liner and filter are two separable pieces, said liner is reusable and said filter is disposable.

12. The combination as defined in claim 8, wherein said bottom filter is microcloth.

13. The combination as defined in claim 12, wherein said support members include a bottom rim extending completely around said microcloth filter and other support members extend across said microcloth filter to sandwich said microcloth therebetween.

14. The apparatus as recited in claim 1, wherein said liner and filter are constructed of one piece and disposable.

15. The apparatus as recited in claim 1, wherein said liner and filter are two separable pieces, said liner is reusable and said filter is disposable.

16. An apparatus for filtering tissue float bath water in a heated container, comprising:
   a removable filter for filtering said tissue float bath water, said filter having a flat microcloth bottom;
   a plurality of support members extending across said flat microcloth bottom for sandwiching said microcloth bottom therebetween and providing support to said filter;

a bottom rim extending around said microcloth bottom and connecting to said plurality of support members; and a removable liner for lining said tissue float water bath container and having at least one top attachment means for securely attaching said removable liner to said tissue float water bath container and at least one bottom attachment means for attaching said removable liner to said filter, said top attachment means including an adhesive tab, and said bottom attachment means being pressure fit so said filter can be quickly released and discarded.

* * * * *